(12) United States Patent
Tarng et al.

(10) Patent No.: US 12,064,128 B2
(45) Date of Patent: Aug. 20, 2024

(54) ASSEMBLING KIT FOR INSTALLING INTRAMEDULLARY NAIL

(71) Applicant: METAL INDUSTRIES RESEARCH & DEVELOPMENT CENTRE, Kaohsiung (TW)

(72) Inventors: Yih-Wen Tarng, Kaohsiung (TW); Bing-Feng Huang, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 377 days.

(21) Appl. No.: 17/644,781

(22) Filed: Dec. 16, 2021

(65) Prior Publication Data
US 2023/0190311 A1 Jun. 22, 2023

(51) Int. Cl.
*A61B 17/17* (2006.01)
(52) U.S. Cl.
CPC ...... *A61B 17/1717* (2013.01); *A61B 17/1703* (2013.01)
(58) Field of Classification Search
CPC .. A61B 17/17; A61B 17/1703; A61B 17/1717
See application file for complete search history.

(56) References Cited

U.S. PATENT DOCUMENTS

| | | | | |
|---|---|---|---|---|
| 2008/0275566 A1* | 11/2008 | Lewis | ............... | A61B 17/1637 606/100 |
| 2010/0130978 A1* | 5/2010 | Orbay | ............... | A61F 2/4261 606/62 |
| 2017/0112552 A1* | 4/2017 | Sinnott | ............... | A61B 17/863 |

FOREIGN PATENT DOCUMENTS

| | | |
|---|---|---|
| TW | M306498 U | 2/2007 |
| TW | 418328 B | 12/2013 |
| TW | 563963 B | 1/2017 |
| TW | 201703731 A | 2/2017 |
| TW | 686168 B | 3/2020 |

* cited by examiner

*Primary Examiner* — Christopher J Beccia
(74) *Attorney, Agent, or Firm* — CKC & Partners Co., LLC

(57) ABSTRACT

An assembling kit for installing intramedullary nail is provided, which is suitable for assisting in fixing a securing member to at least one fixing hole of an intramedullary nail placed in a bone. The assembling kit for installing intramedullary nail includes a drilling member, a guiding member and a hole-reaming member. The drilling member is configured to form an opening on a surface of the bone and has a tapping portion. A diameter of the tapping portion is greater than a diameter of the fixing hole. The guiding member is configured to be put into the fixing hole along a central axis. The hole-reaming member is sleeved on the guiding member and is configured to ream the opening to form a mounting hole. The hole-reaming member has a reaming portion, and a diameter of the reaming portion is greater than the diameter of the tapping portion.

8 Claims, 6 Drawing Sheets

ASSEMBLING KIT FOR INSTALLING INTRAMEDULLARY NAIL

BACKGROUND

Field of Invention

The present invention relates to an assembling kit. More particularly, the present invention relates to an assembling kit for installing an intramedullary nail.

Description of Related Art

An intramedullary nail is equipment which can be implanted in the medullary cavities of fractured bones and installed between fractured bones to fix the fractured bones. After determining the position of the intramedullary nail, the operator will secure the securing member to the opposite ends of the intramedullary nail to fix the intramedullary nail.

However, while the intramedullary nail is being inserted into the medullary cavity from a proximal end of the human body, it might be slightly offset or deformed during the inserting process, and thus it is difficult for the operator to know where fixing holes are actually located on the intramedullary nail near a distal end of the human body.

Therefore, how to help operators correctly know the fixing holes of intramedullary nails and shorten the installation time of intramedullary nails has become a goal for relevant industries to develop relevant products.

SUMMARY

An object of the invention is to provide an assembling kit for installing an intramedullary nail to solve the aforementioned problem.

According to the aforementioned object, an assembling kit for installing intramedullary nail is provided. The assembling kit for installing intramedullary nail is suitable for assisting in fixing a securing member to an intramedullary nail which is placed in a medullary cavity of a bone. The Intramedullary nail has at least one fixing hole. The assembling kit for installing intramedullary nail includes a drilling member, a guiding member and a hole-reaming member. The drilling member is configured to form an opening on a surface of the bone, in which the drilling member has a tapping portion, and a diameter of the tapping portion is greater than a diameter of the at least one fixing hole. The guiding member is configured to be put into the at least one fixing hole along a central axis of the at least one fixing hole. The hole-reaming member is sleeved on the guiding member, in which the hole-reaming member is configured to ream the opening to form a mounting hole, in which the hole-reaming member has a reaming portion, and a diameter of the reaming portion is greater than the diameter of the tapping portion.

According to an embodiment of the present invention, the guiding member includes a positioning portion and a guiding rod connected to the positioning portion, in which an external diameter and a shape of the positioning portion correspond to the at least one fixing hole, and an extending direction of the guiding rod overlaps the central axis of the at least one fixing hole.

According to an embodiment of the present invention, the assembling kit for installing intramedullary nail further includes an expansion member configured to be disposed in the mounting hole, in which the expansion member has a through hole, and an outer surface of the expansion member are set with a plurality of grooves.

According to an embodiment of the present invention, the securing member has a head portion and a rod portion connected to the head portion, in which the rod portion is put through the at least one fixing hole and is fixed to another surface of the bone, and the head portion is constrained in the through hole of the expansion member.

According to an embodiment of the present invention, the head portion is a tapered structure, and an outer surface of the head portion is abutted against an inner surface of the mounting hole.

According to an embodiment of the present invention, a dimension of the head portion gradually increases along a direction which is opposite to a securing direction of the securing member.

According to an embodiment of the present invention, the tapping portion of the drilling member is formed by threads and has a tip end portion.

According to an embodiment of the present invention, the reaming portion of the hole-reaming member is formed by threads and has an arc-shaped end portion.

According to an embodiment of the present invention, the hole-reaming member is a hollow screw which has a hollow passage, in which the hollow passage is configured to enable the guiding member to be passed through.

According to an embodiment of the present invention, the assembling kit for installing intramedullary nail includes an image capturing device configured to capture an image of the at least one fixing hole of the Intramedullary nail.

According to the aforementioned embodiments of the present disclosure, the assembling kit for installing intramedullary nail of the present disclosure is used to assist the operator to fix the securing member to the intramedullary nail in the medullary cavity in a correct direction without significantly changing the existing operating process. Therefore, the operator does not need to use a conventional lighting to find the location of the fixing hole, thereby saving a lot of operating time. In addition, by using the assembling kit for installing intramedullary nail of the present disclosure may also help the operator quickly form a mounting hole on the surface of the bone, and the mounting hole is further used to guide the securing member to be fixed at in a proper position at a correct angle, thereby improving the overall operating efficiency and reliability.

BRIEF DESCRIPTION OF THE DRAWINGS

The invention can be more fully understood by reading the following detailed description of the embodiment, with reference made to the accompanying drawings as follows.

DETAILED DESCRIPTION

Figure 2:
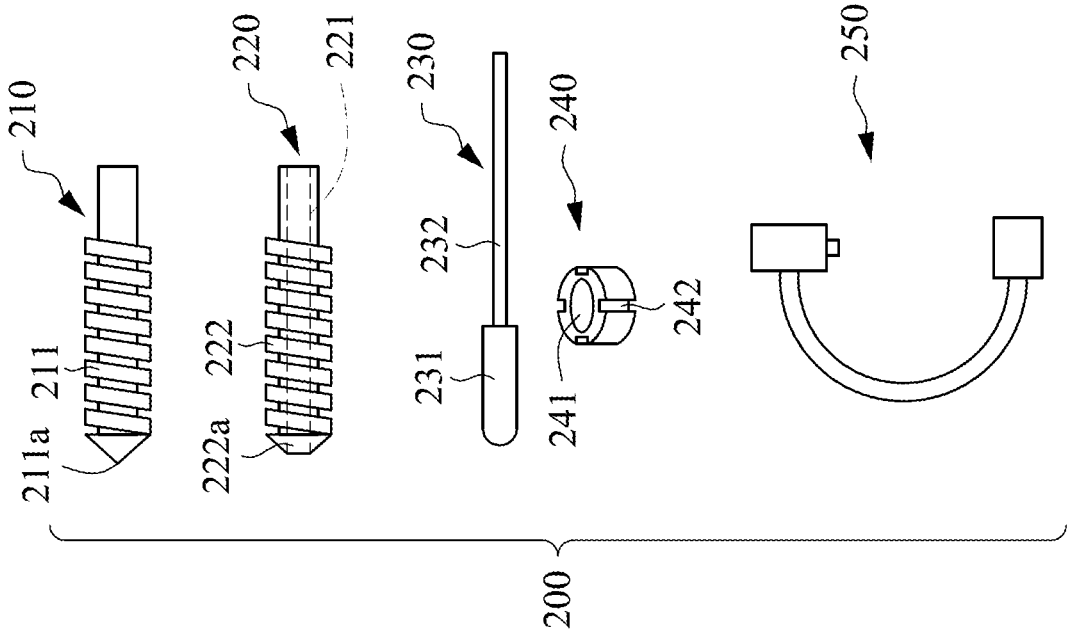
FIG. 2 is a schematic partial structural diagram showing an assembling kit for installing intramedullary nail according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

Figure 1:
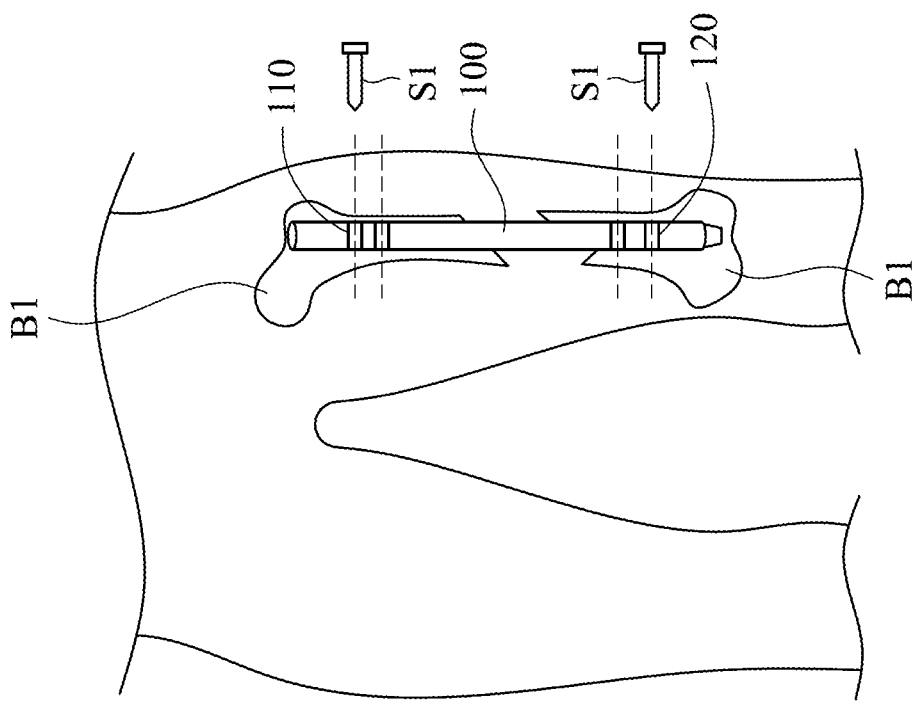
FIG. 1 is a schematic diagram showing an intramedullary nail placed in a femur in accordance with an embodiment of the present invention.

Simultaneously referring to FIG. 1 and FIG. 2, FIG. 1 is a schematic diagram showing an intramedullary nail 100 placed in a femur in accordance with an embodiment of the present invention, and FIG. 2 is a schematic partial structural diagram showing an assembling kit for installing intramedullary nail according to an embodiment of the present invention. As shown in FIG. 1, when a bone B1 (for example, a human's femur) is fractured, the operator first forms an opening from a surface of human's thigh through the femur at a location on the thigh near a human's heart (a proximal end of the human body). Thereafter, the operator then inserts the intramedullary nail 100 into a medullary cavity of the femur from the proximal end, and meanwhile operator slowly pushes the intramedullary nail 100 toward a location away from the human's heart (a distal end of the human body) to a predetermined position located between two adjacent fractured bones of the femur. When the intramedullary nail 100 has arrived at the predetermined position, the operator further fixes the securing members S1 to a fixing hole 110 near the proximal end and a fixing hole 120 near the distal end of the Intramedullary nail 100, so as to stabilize the intramedullary nail 100. However, since Intramedullary nail 100 is inserted into the femur from the opening near the proximal end of the thigh, the operator can directly see the position of fixing hole 110 of the intramedullary nail 100 near the proximal end, but cannot see the actual position of the fixing hole 120 of the intramedullary nail 100 near the distal end. Therefore, the assembling kit for installing intramedullary nail 200 of the present embodiment can be used to assist the operator to correctly fix the securing member S1 to the fixing hole 120 of intramedullary nail 100 near the distal end.

As shown in FIG. 2, the assembling kit for installing intramedullary nail 200 mainly includes a drilling member 210, a hole-reaming member 220 and a guiding member 230. In other embodiments, the assembling kit for installing intramedullary nail 200 may further include an expansion member 240 and an image capturing device 250. In other words, the expansion member 240 and the image capturing device 250 are optional components, which can be used or not used depending on operator's requirements. In the present invention, an external diameter of the drilling member 210 is greater than a hole diameter of the fixing hole 120, and an external diameter of the hole-reaming member 220 is greater than an external diameter of the drilling member 210.

Figure 3B:
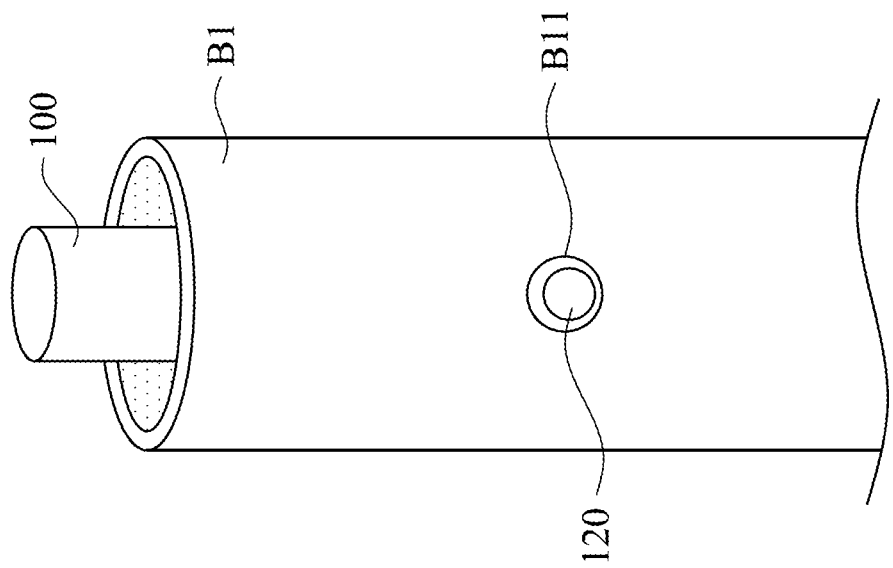
FIG. 3A-FIG. 8 are schematic diagrams showing a usage process according to an embodiment of the present invention.
Figure 3A:
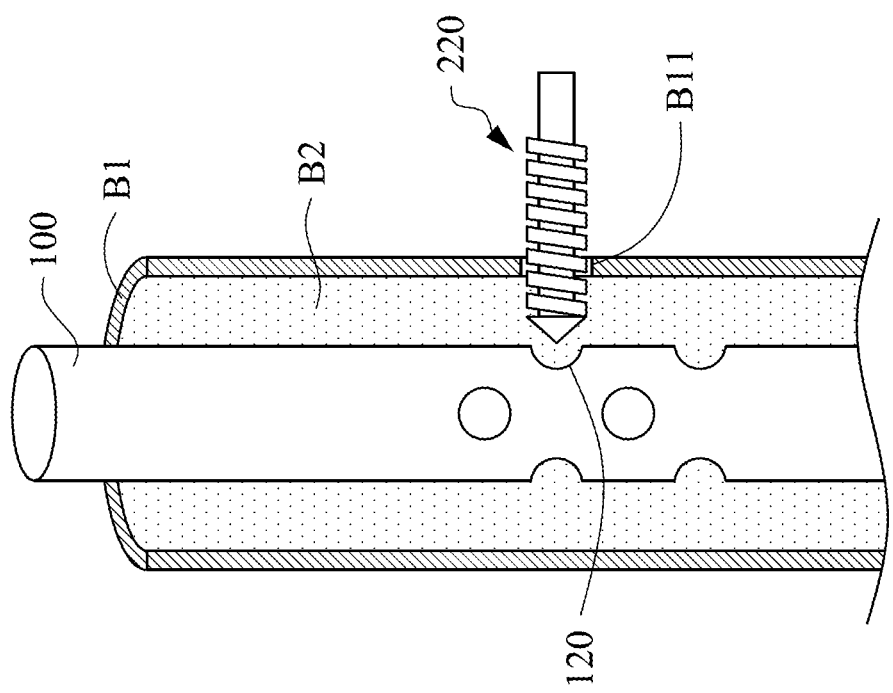

Referring to FIG. 3A, FIG. 3A is a schematic diagram showing the drilling member 210 in a use state according to an embodiment of the present invention. As shown in FIG. 3A, the bone B1 inherently has a medullary cavity B2. The intramedullary nail 100 is placed in the medullary cavity B2, and the intramedullary nail 100 has at least one fixing hole 120 at the distal end. In one embodiment, there are multiple fixing holes 120 disposed on the distal end of the intramedullary nail 100, and these fixing holes 120 face in different directions. In the present embodiment, the drilling member 210 is configured to form an opening B11 on a surface of the bone B1. More specifically, the drilling member 210 has a tapping portion 211, and the tapping portion 211 is formed by threads and has a tip end portion 211a, which enables the drilling member 210 to drill into the bone B1 from the surface of the bone B1 and penetrate into the medullary cavity B2 of the bone B1, thereby exposing the fixing hole 120 of the Intramedullary nail 100. Simultaneously referring to FIG. 3B, FIG. 3B is a schematic diagram showing the opening B11 formed on the surface of the bone B1 according to an embodiment of the present invention. Because a diameter of the tapping portion 211 of the drilling member 210 is greater than the hole diameter of the fixing hole 120, the opening range of the hole B11 formed by the drilling member 210 covers the opening range of the fixing hole 120. In a situation, when an experienced operator uses the drilling member 210 to form the opening B11 on the surface of the bone B1, he is able to directly determine a drilling position of the drilling member 210 on the surface of the bone B1 according to the length and the placement angle of the intramedullary nail 100. In other situations, before drilling, the operator may also use the image capturing device 250 to obtain an image of the Intramedullary nail 100 with the fixing hole 120, so as to grasp an actual position of the fixing hole 120, thereby determining the drilling position on the surface of the bone B1. In one embodiment, the image capturing device 250 is a C-arm fluoroscopy x-ray machine.

Figure 4:
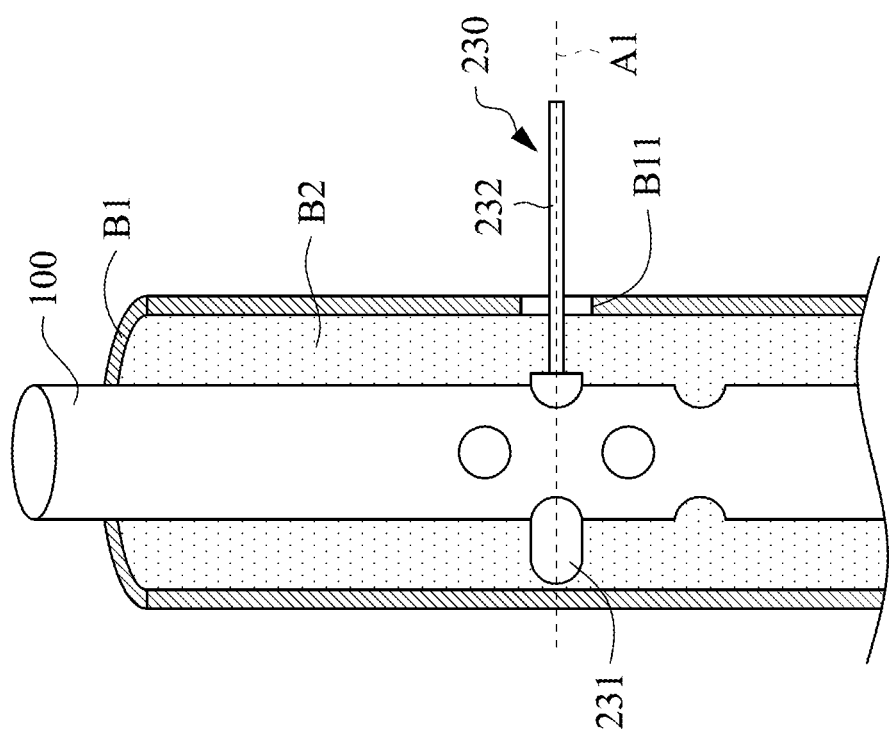

Simultaneously referring to FIG. 3A and FIG. 4, FIG. 4 is a schematic diagram showing the guiding member 230 in a use state according to an embodiment of the present invention. The guiding member 230 is configured to be passed through the fixing hole 120 along a central axis A1 of the fixing hole 120. The guiding member 230 includes a positioning portion 231 and a guiding rod 232, and the guiding rod 232 is connected to the positioning portion 231. An external diameter and a shape of the positioning portion 231 are corresponded to those of the fixing hole 120, and the guiding rod 232 extends along the central axis A1. Therefore, the positioning portion 231 of the guiding member 230 can be inserted from the opening B11 and further be positioned in the fixing hole 120, such that that a portion of the guiding rod 232 is extended outside the bone B1. Since the shape of the positioning portion 231 is matched with the fixing hole 120, as long as the positioning portion 231 is inserted into the fixing hole 120, it can be ensured that the extending direction of the guiding rod 232 overlaps with the central axis A1 of the fixing hole 120.

Figure 5:
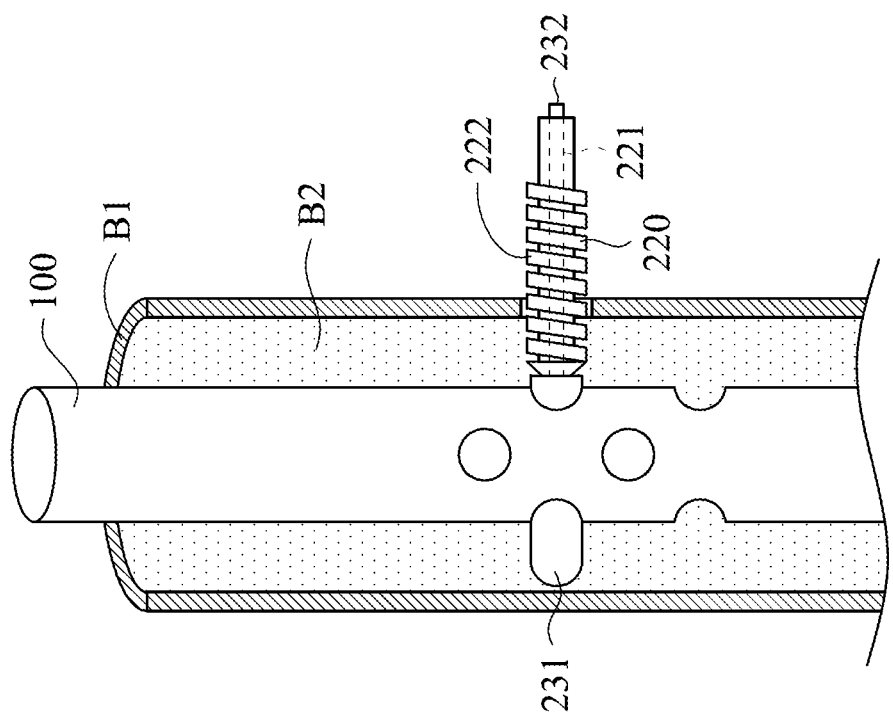
Figure 6:
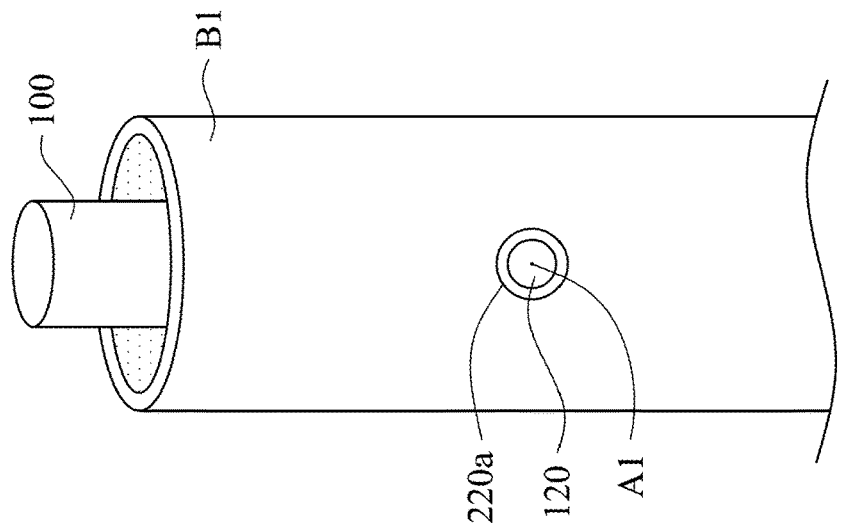

Simultaneously referring to FIG. 4 and FIG. 5, FIG. 5 is a schematic diagram showing the hole-reaming member 220 in a use state according to an embodiment of the present invention. The hole-reaming member 220 is a hollow structure and has a hollow passage 221 and a reaming portion 222. The reaming portion 222 is formed by threads and has an arc-shaped end portion 222a. As shown in FIG. 5, the hole-reaming member 220 is configured to be sleeved on the guiding member 230 by its hollow passage 221. Moreover, a diameter of the reaming portion 222 of the hole-reaming member 220 is greater than the diameter of the drilling member 210, thereby enabling the reaming portion 222 to ream and enlarge the opening B11 to form a mounting hole 220a. More specifically, because the hole-reaming member 220 is sleeved on the guiding rod 232 of the guiding member 230, the hole-reaming member 220 can be constrained by the guiding rod 232 to move only along the central axis A1 of the fixing hole 120 and ream the opening B11 at the same time, and the reamed opening B11 can be used as the mounting hole 220a. In some embodiments, an inner diameter of the hollow passage 221 of the hole-reaming member 220 is designed corresponding to a width of the guiding rod 232 of the guiding member 230, thereby ensuring the hole-reaming member 220 to stably move on the guiding rod 232. Simultaneously referring to FIG. 6, FIG. 6 is a schematic diagram showing the mounting hole 220a formed on the surface of the bone B1 according to an embodiment of the present invention, and a center of the mounting hole 220a is located on the central axis A1 of the fixing hole 120.

Therefore, the mounting hole 220*a* can be used to guide and allow the securing member S1 as shown in FIG. 1 to pass therein, so as to ensure that the securing member S1 can be fixed in the fixing hole 120 along the central axis A1 of the fixing hole 120.

Figure 7B:
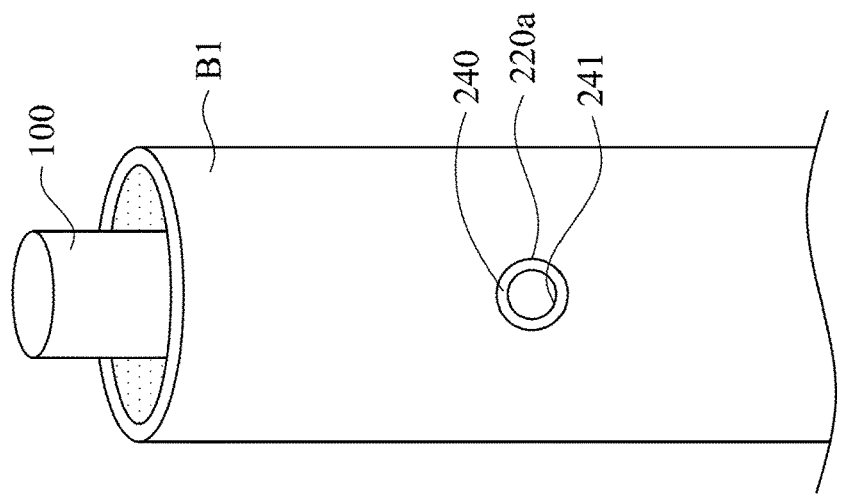
Figure 7A:
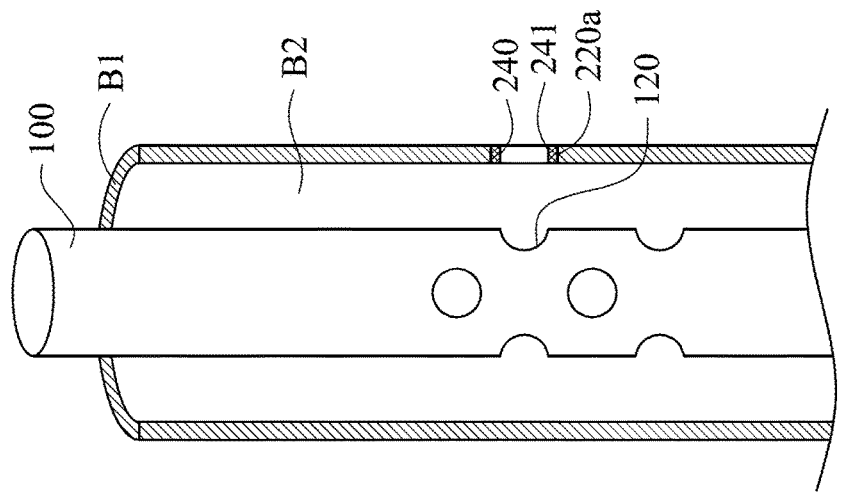

Referring to FIG. 7A and FIG. 7B, FIG. 7A and FIG. 7B are schematic diagrams showing the expansion member 240 in a use state according to an embodiment of the present invention. In one embodiment, after the mounting hole 220*a* is formed, the expansion member 240 can be disposed in the mounting hole 220*a*. The expansion member 240 is an element which is elastic and can be deformed by an external force. As shown in FIG. 2, the expansion member 240 has a through hole 241 and plural grooves 242 on its surface.

Figure 8:
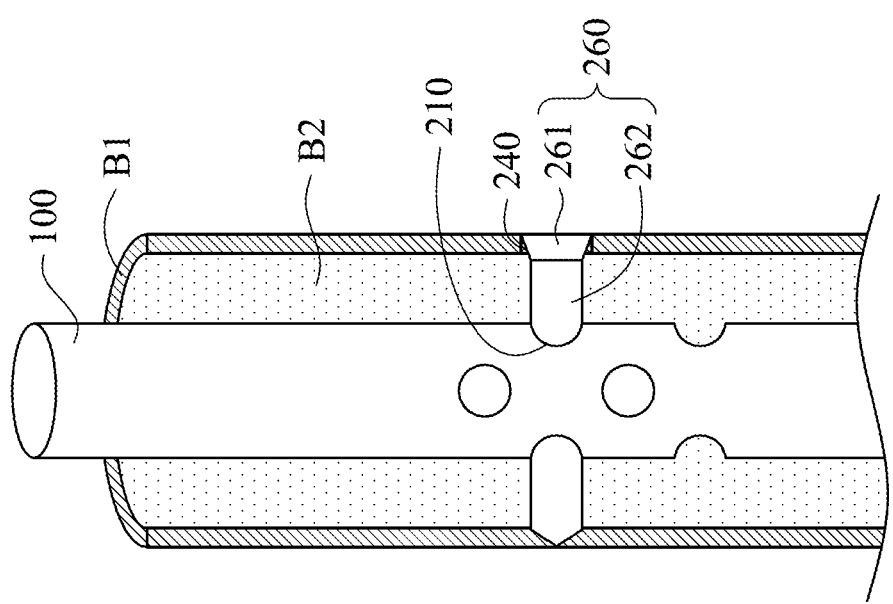

Simultaneously referring to FIG. 7A to FIG. 8, FIG. 8 is a schematic diagram showing the expansion member 240 in a use state according to an embodiment of the present invention. After the expansion member 240 is disposed in the mounting hole 220*a*, the securing member 260 can be fixed to the fixing hole 120 of the intramedullary nail 100. As shown in FIG. 8, the securing member 260 has a head portion 261 and a rod portion 262 connected to the head portion 261. The rod portion 262 passes through the fixing hole 120 and is fixed to another surface of the bone B1, and the head portion 261 is constrained in the through hole 241 of the expansion member 240. In one embodiment, the head portion 261 of the securing member 260 is a tapered structure, and the outer surface of the head portion 261 is abutted against the inner surface of the through hole 241, meanwhile, the outer surface of the expansion member 240 is abutted against the inner surface of the mounting hole 220*a*. In one embodiment, the external diameter of the head portion 261 gradually increases along a direction opposite to the securing direction of the securing member 260. In one embodiment, the outer surface of the head portion 261 is an inclined surface, while the securing member 260 is being securing to the intramedullary nail 100, the force acted on the expansion member 240 by the head portion 261 having gradually changing dimensions is gradually increased, so that the expansion member 240 can be tightly abutted against the inner surface of mounting hole 220*a*. In one embodiment, the outer surface of the expansion member 240 has plural grooves 242, and the grooves 242 provide a compression space when the expansion member 240 is expanded.

In some situations, if the size of the head portion 261 of the securing member 260 is matched with the inner diameter of the mounting hole 220*a*, the expansion member 240 may be omitted. It is only necessary to insert and fix the securing member 260 into the fixing hole 120, and confine the head portion 261 within the mounting hole 220*a*.

Figure 9:
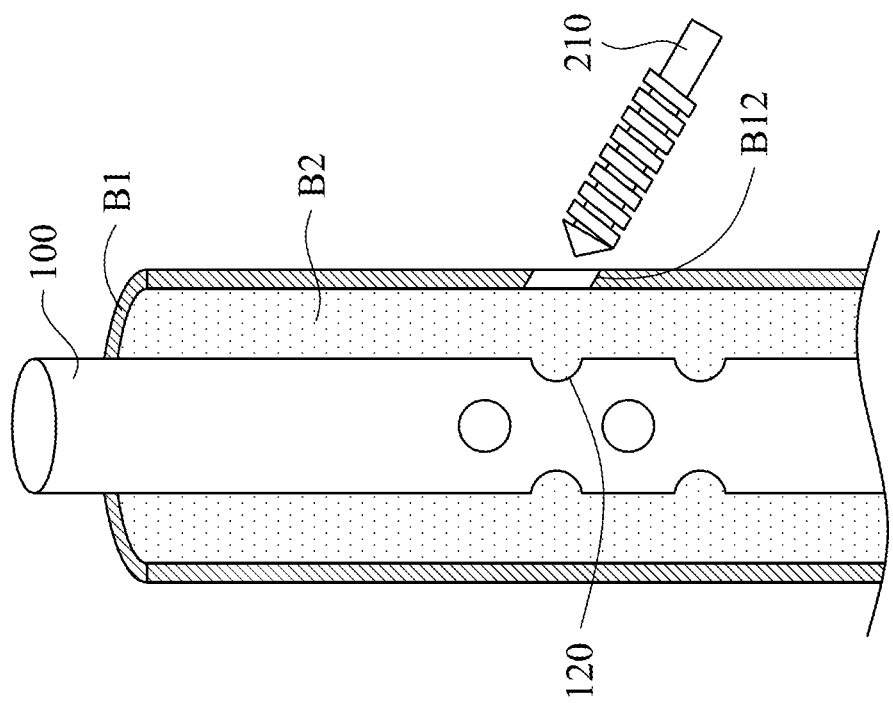
FIG. 9-FIG. 11 are other schematic diagrams showing a usage process according to an embodiment of the present invention.
Figure 11:
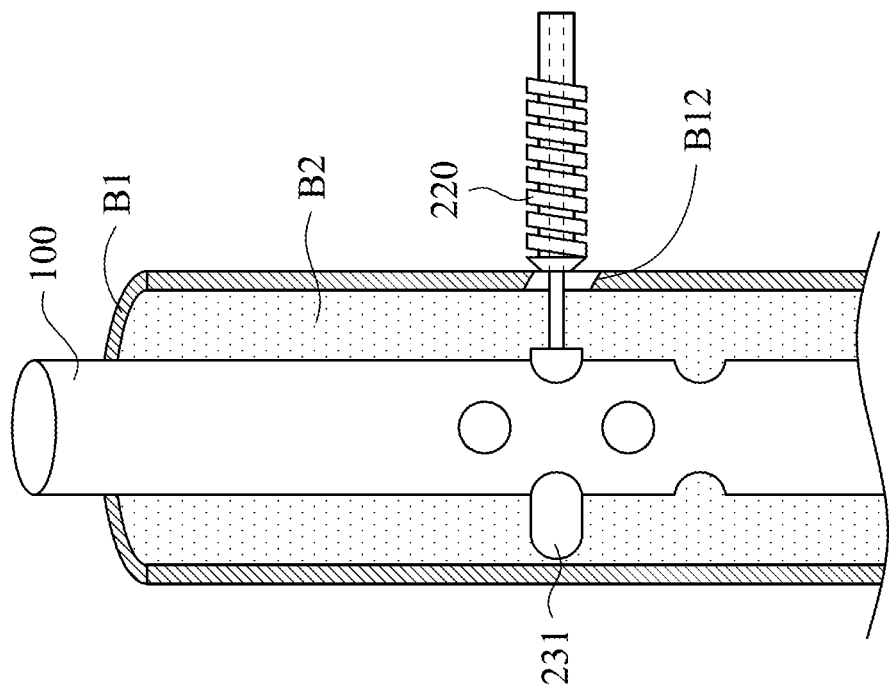
Figure 10:
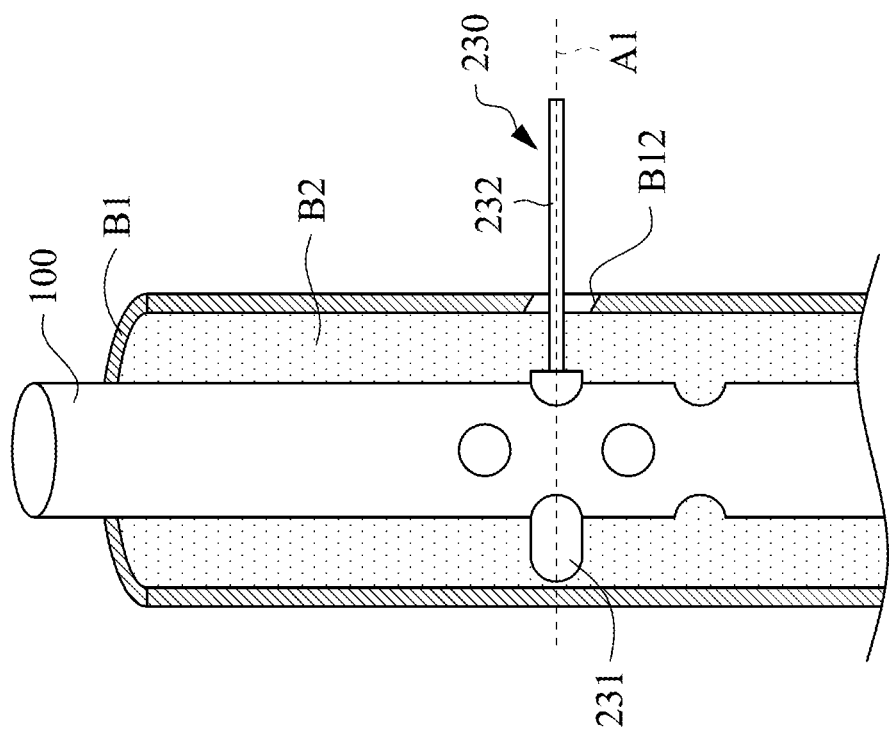

The assembling kit for installing intramedullary nail 200 of the present disclosure may be used in different ways. Simultaneously referring to FIG. 2 and FIG. 9 to FIG. 11, in which FIG. 9 to FIG. 11 are other schematic diagrams showing a usage process according to an embodiment of the present invention. When the opening B12 on the surface of bone B1 formed by the drilling member 210 is an oblique hole, which will not affect the overall operation of assembling kit for installing intramedullary nail 200. As mentioned above, under the premise of knowing an approximate location of the fixing hole 120 of intramedullary nail 100, the operator only needs to use the drilling member 210 to from the opening B12 on the surface of bone B1 that can cover the opening range of the fixing hole 120, so as to expose the fixing hole 120 of intramedullary nail 100. Then, the operator can further use the guiding member 230 to penetrate into the fixing hole 120. While the positioning portion 231 of the guiding member 230 is positioned in the fixing hole 120, it can be ensured that the extending direction of the guiding rod 232 overlaps with the central axis A1 of the fixing hole 120. Meanwhile, the operator can sleeve the hole-reaming member 220 around the guiding member 230 and move the hole-reaming member 220 to ream the opening B12, thereby forming a mounting hole. Therefore, a securing member can be fixed to the fixing hole 120 along the central axis A1 of the fixing hole 120. In one embodiment, the hole-reaming member 220 which has a greater external diameter than the hole diameter of the opening B12 can be used to form the mounting hole.

According to the aforementioned embodiments of the present disclosure, the assembling kit for installing intramedullary nail of the present disclosure is used to assist the operator to fix the securing member to the intramedullary nail in the medullary cavity in a correct direction without significantly changing the existing operating process. Therefore, the operator does not need to use a conventional lighting to find the location of the fixing hole, thereby saving a lot of operating time. In addition, by using the assembling kit for installing intramedullary nail of the present disclosure may also help the operator quickly form a mounting hole on the surface of the bone, and the mounting hole is further used to guide the securing member to be fixed at in a proper position at a correct angle, thereby improving the overall operating efficiency and reliability.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An assembling kit for installing intramedullary nail, which is suitable for assisting in fixing a securing member to an intramedullary nail which is placed in a medullary cavity of a bone, wherein the Intramedullary nail has at least one fixing hole, and the assembling kit for installing intramedullary nail comprises:
   a drilling member configured to form an opening on a surface of the bone, wherein the drilling member has a tapping portion, and a diameter of the tapping portion is greater than a diameter of the at least one fixing hole;
   a guiding member configured to be put into the at least one fixing hole along a central axis of the at least one fixing hole;
   a hole-reaming member sleeved on the guiding member, wherein the hole-reaming member is configured to ream the opening to form a mounting hole, wherein the hole-reaming member has a reaming portion, and a diameter of the reaming portion is greater than the diameter of the tapping portion; and
   an expansion member configured to be disposed in the mounting hole, wherein the expansion member has a through hole, and an outer surface of the expansion member are set with a plurality of grooves,
   wherein the securing member has a head portion and a rod portion connected to the head portion, wherein the rod portion is put through the at least one fixing hole and is fixed to another surface of the bone, and the head portion is constrained in the through hole of the expansion member.

2. The assembling kit for installing intramedullary nail of claim 1, wherein the guiding member comprises a positioning portion and a guiding rod connected to the positioning portion, wherein an external diameter and a shape of the positioning portion correspond to the at least one fixing hole, and an extending direction of the guiding rod overlaps the central axis of the at least one fixing hole.

3. The assembling kit for installing intramedullary nail of claim 1, wherein the head portion is a tapered structure, and an outer surface of the head portion is abutted against an inner surface of the mounting hole.

4. The assembling kit for installing intramedullary nail of claim 1, wherein a dimension of the head portion gradually increases along a direction which is opposite to a securing direction of the securing member.

5. The assembling kit for installing intramedullary nail of claim 1, wherein the tapping portion of the drilling member is formed by threads and has a tip end portion.

6. The assembling kit for installing intramedullary nail of claim 1, wherein the reaming portion of the hole-reaming member is formed by threads and has an arc-shaped end portion.

7. The assembling kit for installing intramedullary nail of claim 1, wherein the hole-reaming member is a hollow screw which has a hollow passage, wherein the hollow passage is configured to enable the guiding member to be passed through.

8. The assembling kit for installing intramedullary nail of claim 1, further comprises an image capturing device configured to capture an image of the at least one fixing hole of the Intramedullary nail.

\* \* \* \* \*